US011850362B2

(12) United States Patent
Dhara (10) Patent No.: US 11,850,362 B2
(45) Date of Patent: Dec. 26, 2023

(54) ENDOTRACHEAL TUBE AND METHOD OF USE

(71) Applicant: Naga Wire-Tracking Tracheal Tube PTY LTD, Sandy Bay (AU)

(72) Inventor: Sasanka Sekhar Dhara, Sandy Bay (AU)

(73) Assignee: Naga Wire-Tracking Tracheal Tube PTY LTD, Sandy Bay (AU)

( * ) Notice: Subject to any disclaimer, the term of this patent is extended or adjusted under 35 U.S.C. 154(b) by 544 days.

(21) Appl. No.: 16/795,412

(22) Filed: Feb. 19, 2020

(65) Prior Publication Data

US 2020/0197643 A1    Jun. 25, 2020

Related U.S. Application Data

(63) Continuation of application No. 14/917,540, filed as application No. PCT/AU2014/000784 on Aug. 5, 2014, now abandoned.

(30) Foreign Application Priority Data

Sep. 23, 2013   (AU) .................................. 2013903646
Apr. 11, 2014   (AU) .................................. 2014901331

(51) Int. Cl.
*A61M 16/04*    (2006.01)
*A61M 16/01*    (2006.01)
(52) U.S. Cl.
CPC ........ *A61M 16/0488* (2013.01); *A61M 16/01* (2013.01); *A61M 16/0411* (2014.02);
(Continued)

(58) Field of Classification Search
CPC .............. A61M 16/0488; A61M 16/01; A61M 16/0411; A61M 16/0434; A61M 16/0461;
(Continued)

(56) References Cited

U.S. PATENT DOCUMENTS 4,150,676 A * 4/1979 Jackson ................ A61M 16/04
                                                        128/207.18
4,170,232 A   10/1979 Khoury
(Continued)

FOREIGN PATENT DOCUMENTS

AU    2013903646    10/2013
AU    2014901331     4/2014
(Continued)

OTHER PUBLICATIONS

Amended Sheets for PCT/AU2014/00784 received Feb. 7, 2015.
(Continued)

*Primary Examiner* — Annette Dixon
(74) *Attorney, Agent, or Firm* — TraskBritt (57) ABSTRACT

This disclosure provides an endotracheal tube with a tip suitable for traversing the laryngeal inlet and with a guiding channel having a proximal opening adjacent a proximal end portion and a distal opening adjacent to a tip, wherein the guiding channel is adjacent a sidewall of the main lumen of the tube, which allows more accurate wire-guided intubation of a patient, a method and a kit relating to the same.

9 Claims, 3 Drawing Sheets

(52) U.S. Cl.
CPC .... *A61M 16/0434* (2013.01); *A61M 16/0461* (2013.01); *A61M 16/0486* (2014.02); *A61M 2016/0413* (2013.01); *A61M 2207/00* (2013.01); *A61M 2209/06* (2013.01); *A61M 2230/432* (2013.01)

(58) Field of Classification Search
CPC ...... A61M 16/0486; A61 2016/0413; A61M 2207/00; A61M 2209/06; A61M 2230/432; A61M 16/0484; A61M 1/008; A61M 1/84; A61M 16/0003; A61M 16/0084; A61M 16/04; A61M 16/0409; A61M 16/0415; A61M 16/0418; A61M 16/0425; A61M 16/0427; A61M 16/0429; A61M 16/0431; A61M 16/044; A61M 16/0445; A61M 16/0456; A61M 16/0459; A61M 16/0463; A61M 16/0465; A61M 16/0472; A61M 16/0479; A61M 16/0493; A61M 16/0495; A61M 16/0497; A61M 16/06; A61M 16/0605; A61M 16/0666; A61M 16/08; A61M 16/085; A61M 16/1015; A61M 2025/0081; A61M 2205/0222; A61M 2205/0238; A61M 2205/32; A61M 2205/6054; A61M 2210/0618; A61M 2210/1053; A61M 2230/005; A61M 25/005; A61M 25/0053; A61M 25/0054; A61M 25/0068; A61M 25/0069; A61M 25/008; A61M 25/0082; A61M 25/0147; A61M 25/0152; A61M 25/09; A61M 25/09025; A61M 25/09033; A61M 25/10; A61B 1/00016; A61B 1/00064; A61B 1/00078; A61B 1/00135; A61B 1/00137; A61B 1/0014; A61B 1/00142; A61B 1/00154; A61B 1/00165; A61B 1/015; A61B 1/018; A61B 1/05; A61B 1/06; A61B 1/07; A61B 1/233; A61B 1/267; A61B 1/2673; A61B 1/2676; A61B 1/303; A61B 17/24; A61B 17/3417; A61B 17/3468; A61F 2/02; A61F 2/20; A61F 2/203; A61F 2002/046; A61F 6/005; A61F 6/22; C10M 2209/104; Y10S 128/911; Y10S 128/912; Y10S 2/908
See application file for complete search history.

(56) References Cited

U.S. PATENT DOCUMENTS

| | | | |
|---|---|---|---|
| 4,337,761 A * | 7/1982 | Upsher | A61B 1/07 600/196 |
| 4,509,945 A * | 4/1985 | Kramann | A61M 25/0111 604/164.13 |
| 4,530,354 A | 7/1985 | Froilan | |
| 4,589,410 A * | 5/1986 | Miller | A61M 16/04 D24/129 |
| 4,637,389 A | 1/1987 | Heyden | |
| 4,672,960 A * | 6/1987 | Frankel | A61M 16/0415 128/207.14 |
| 4,737,153 A * | 4/1988 | Shimamura | A61M 16/0425 138/131 |
| 4,793,327 A | 12/1988 | Frankel | |
| 4,913,139 A | 4/1990 | Ballew | |
| 5,269,769 A | 12/1993 | Dhara et al. | |
| 5,507,279 A * | 4/1996 | Fortune | A61M 16/0472 128/207.29 |
| 5,588,424 A | 12/1996 | Insler et al. | |
| 6,321,749 B1 | 11/2001 | Toti et al. | |
| 6,463,927 B1 | 10/2002 | Pagan | |
| 6,553,993 B2 | 4/2003 | Toti et al. | |
| 6,761,171 B2 | 7/2004 | Toti et al. | |
| 7,921,847 B2 | 4/2011 | Totz | |
| 8,231,606 B2 | 7/2012 | Stenzler et al. | |
| 2002/0043266 A1 | 4/2002 | Toti et al. | |
| 2002/0096177 A1 | 7/2002 | Toti et al. | |
| 2003/0062039 A1 | 4/2003 | Sniadach | |
| 2004/0139972 A1 | 7/2004 | Wong et al. | |
| 2006/0076022 A1 | 4/2006 | Dauri et al. | |
| 2006/0081253 A1 | 4/2006 | Nelson | |
| 2007/0017527 A1 | 1/2007 | Totz | |
| 2009/0071484 A1 | 3/2009 | Black et al. | |
| 2009/0107503 A1 | 4/2009 | Baran | |
| 2009/0125002 A1 | 5/2009 | Totz | |
| 2009/0229615 A1 | 9/2009 | Stenzler et al. | |
| 2010/0113916 A1 | 5/2010 | Kumar | |
| 2010/0191054 A1 * | 7/2010 | Supiez | A61B 1/00154 128/207.14 |
| 2010/0288289 A1 * | 11/2010 | Nasir | A61M 16/0493 128/207.14 |
| 2011/0030680 A1 | 2/2011 | Wood et al. | |
| 2011/0315147 A1 | 12/2011 | Wood et al. | |
| 2012/0180787 A1 | 7/2012 | Bosel | |

FOREIGN PATENT DOCUMENTS

| | | |
|---|---|---|
| CN | 2395734 Y | 9/2000 |
| CN | 2452528 Y | 10/2001 |
| CN | 202096565 U | 1/2012 |
| CN | 102813990 A | 12/2012 |
| DE | 29814396 U1 | 11/1998 |
| EP | 0102422 A1 | 3/1984 |
| EP | 0232864 A2 | 8/1987 |
| JP | 62-281961 A | 12/1987 |
| JP | 63-003841 U | 1/1988 |
| JP | 2006-527027 A | 11/2006 |
| WO | 93/24161 A1 | 12/1993 |
| WO | 03/45485 A1 | 6/2003 |
| WO | 2003/101515 A1 | 12/2003 |
| WO | 2004/108187 A2 | 12/2004 |
| WO | 2009/114455 A2 | 9/2009 |
| WO | 2010/080746 A2 | 7/2010 |
| WO | 2012/005850 A1 | 1/2012 |
| WO | 2015/039164 A1 | 3/2015 |

OTHER PUBLICATIONS

Australian Patent Examination Report No. 1 for Australian Application No. 2014324068, dated Mar. 7, 2019, 04 pages.
Brull SJ, Wiklund R, Ferris C, Connelly NR, Ehrenworth J, Silverman DG. Facilitation of fibreoptic orotracheal intubation with a flexible tracheal tube. Anesth Analg 1994; 78; 746-8.
Chinese First Office Action for Chinese Application No. 201480052122, dated Feb. 27, 2017, 19 page.
Chinese Search Report for Chinese Application No. 201480052122, dated Feb. 8, 2017, 1 page.
Chinese Second Office Action for Chinese Application No. 201480052122, dated Nov. 14, 2017, 20 page.
Chinese Supplementary Search Report for Chinese Application No. 201480052122, dated Nov. 2, 2017, 1 page.
Chinese Third Office Action for Chinese Application No. 201480052122, dated Jun. 8, 2018, 13 page.
Cossham PS.Difficult intubation.Br J Anaesth 1985; 57:239.
Dhara et al., Development of a new system for guidewire-assisted tracheal intubation: manikin and cadaver evaluation, Anaesthesia, 2016, pp. 44-49, vol. 71.
Dhara, S.S., Retrograde tracheal intubation, Anaesthesia, 2009, pp. 1094-1104, vol. 64.
European Communication pursuant to Article 94(3) EPC for European Application No. 14845149.5, dated Sep. 24, 2018, 6 pages.
European Intention to grant for European Application No. 14845149. 5, dated Feb. 12, 2020, 05 pages.
European Search and Opinion for European Application No. 14845149, dated May 16, 2017, 9 pages.
Hagberg, Carin A., Current Concepts in the Management of the Difficult Airway, Anesthesiology News, May 2018, 32 pages.

(56) References Cited

OTHER PUBLICATIONS

Higgs A, Swamipillai, Dravid R, Mitchell, Patel A, Popat M. Re-intubation over airway exchange catheters—mind the gap, Anaesthesia, Journal of the Association of Anesthetists of Great Britain and Ireland, 2010, pp. 857-866, vol. 65.
Hodzovic, Latto IP. Single use tracheal introducers may not be fit for purpose. Anaesthesia 2007; 62:1189-90.
Hwan SJ, Kataoka MT, Roberts JBC, Doyle J, Mazer CD. PVC tracheal tubes exert forces and pressures seven to ten times higher than silicone or armoured tracheal tubes—an in vitro study. Can J Anesth 2002;49(9): 986-989.
Japanese Notice of Reasons for Refusal for Japanese Application No. 2016-543263, dated Jul. 2, 2019, 8 pages with English Translation.
Japanese Notice of Reasons for Refusal for Japanese Application No. 2016-543263, dated Jul. 31, 2018, 9 pages with English Translation.
Japanese Search Report for Japanese Application No. 2016-543263, dated Jul. 23, 2018, 22 pages with English Translation.
Japanese Written Opinion for Japanese Application No. 2016-543263, dated Jan. 23, 2019, 6 pages with English Translation.
Moorthy SS, Dierdorf SF. An unusual difficulty in fibreoptic intubation. Anesthesiology 1985; 63: 229.
PCT International Preliminary Report on Patentability for PCT/AU2014/000784 dated Jul. 24, 2015.
PCT International Search Report, PCT/AU2014/000784, dated Sep. 18, 2014.
PCT International Written Opinion, PCT/AU2014/000784, dated Sep. 18, 2014.
Ponnusamy et al., Comparison of laryngeal morbidities with modified reinforced silicone tube intubation guided over a bougie vs. a guidewire: novel assessment with voice analysis, Anaesthesia, Jan. 2, 2018, 8 pages.
Pujari V, Shivanna S, Bevinaguddiah Y. Wire aided reintubation following rigid bronchoscopy: A safe technique. Indian Paediatrics 2012; 49: 983-84.
Rajan GR. Fibreoptic wire-guided transoral and through the LMA intubation technique using modified gum elastic bougie. Anesth Analg 2005; 100:599-600.
Supplementary European Search Report for EP14845149 dated May 8, 2017, 2 pages.
Telford et al., Use of a guide wire and a ureteral dilator as an aid to awake fibreoptic intubation, Anaesthesia, 1994, pp. 691-693, vol. 49.
Warrillow S. Difficult intubation managed using standard laryngeal mask airway, flexible fibreoptic bronchoscope and wire guided enteral feeding tube. Anaesth Intensive Care 2005; 33: 659-661.
Wissler RN, Gravenstein N, Banner MJ. Wire-reinforced endotracheal tubes: composition affects the response to external compression and kinking (Abstract). Anesthesiology 1991; 75 (3A): A394.
Benumof "Additional safety measures when changing endotracheal tubes" Anesthesiology 1991; 75(5):921.
Benumof "Airway exchange catheters for safe extubation—The Clinical and scientific details that make the concept work" Chest (Jun. 1997) 111(6):1483-6.
Bogod et al. NAP4 Report and findings of the 4th National Audit Project of The Royal College of Anaesthetists 2011. Chapter 12 "Tracheal Intubation" pp. 96-104.
Cooper "Use of a LMATM and a sequential technique for unanticipated difficult intubations" Anesthesiology 2002; 97(5):1326.
Evans et al. "Tracheal tube introducers: choose and use with care" Anaesthesia 2010; 65:859.
Gardner et al. "Detachment of the tip of a gum elastic bougie" Anaesthesia 2002; 57:88-89.
Hagberg et al. "Complications of managing the airway" Best Practice & Research Clinical Anaesthesiology (2005) 19(4):641-659.
Hartmannsgruber et al. "Safer endotracheal tube exchange technique" Anesthesiology 1998; 88:1683.
Joffe et al. "Wire guided catheter exchange after failed direct laryngoscopy in critically ill adults" J. Clin. Anesth. 2010; 22:93 5.
Kadry et al. "Pharyngeal wall perforation—an unusual complication of blind intubation with gum elastic bougie" Anaesthesia 1999: 54:404-5.
Lenfant et al. "Comparison of two techniques for retrograde tracheal intubation in human fresh cadavers" Anesthesiology 2006; 104:48 51.
Matioc "Use of the Arndt airway exchanger catheter set with the laryngeal mask airway supreme" J. Clin. Anesth. 2009; 21:152 3.
Prabhu et al. "Bougie trauma—it is still possible" Anaesthesia 2003; 58:811 813.
Scherlitz et al. "Translaryngeal fiber optic insertion of a guidewire into the trachea to assist fiber optic reintubation in patients with a difficult airway" Anaesthesist (1994) 43:618-620 (w/English Abstract).
Stiles "A flexible fiber optic bronchoscope for endotracheal intubation of infants" Anesth. Analg. 1974; 53 (6):1017 1019.
Yurino "Retrograde and antegrade intubation techniques under general anaesthesia through the laryngeal mask airway" J. Clin. Anesth. (1994) 8:227-229.

\* cited by examiner (Scale 2:1)

ENDOTRACHEAL TUBE AND METHOD OF USE

CROSS-REFERENCE TO RELATED APPLICATIONS

This application is a continuation of pending U.S. patent application Ser. No. 14/917,540, filed Mar. 8, 2016, which is a national phase entry under 35 U.S.C. § 371 of International Patent Application PCT/AU2014/000784, filed Aug. 5, 2014, designating the United States of America and published in English as International Patent Publication WO 2015/039164 A1 on Mar. 26, 2015, which claims the benefit under Article 8 of the Patent Cooperation Treaty to Australian Patent Application Serial No. 2014901331, filed Apr. 11, 2014, and to Australian Patent Application Serial No. 2013903646, filed Sep. 23, 2013, the contents of the entirety of each of which are hereby incorporated herein by reference.

TECHNICAL FIELD

This disclosure relates to equipment for use in, and methods of, performing anterograde or retrograde wire-guided endotracheal intubation.

BACKGROUND

An endotracheal tube ("ETT") is normally passed into the trachea of a patient to maintain a patent airway and allow the delivery of oxygen/air/anesthetic gases and vapors to the patient. It may also be used to separate the lungs from the aero-digestive tract and protect from soiling due to aspiration of bodily fluids or to clear respiratory tract of secretions or blood. This is achieved by suction through the ETT. Such procedures may be necessary during resuscitation or general anesthesia, in a patient being treated in an intensive care unit (ICU) or in accident and emergency treatment areas.

Tracheal intubation over a guide wire previously placed inside the larynx or trachea is an alternative method for anticipated or unanticipated difficult intubation.[1-4] The difficulties may arise mainly from anatomical variations, changes caused by disease, trauma, and/or surgical or radio therapeutic treatment in a patient.

The guide wire may be placed in an anterograde (also known as antegrade) way through the mouth or nose and across the laryngeal inlet into the trachea or through a puncture at the space at the front of the neck between the cricothyroid or cricotracheal junctions or upper tracheal rings and advanced upward in a retrograde fashion.[5,6]

Wire-guided intubation is also used for exchange of endotracheal tubes and for trial of extubation in patients who are at a risk of developing an airway obstruction in post-operative period leading to an endotracheal re-intubation.[7-9]

While there are reports of guiding a small tracheal tube directly over a guide wire,[10] the current technique of wire-guided blind tracheal intubation is facilitated by threading a hollow semi-rigid tubular guide over the guide wire to impart an increased diameter and stiffness closer to those of the tracheal tube to be guided over. Custom built exchange catheters (Retrograde Intubation Kit, Cook Medical, USA), fiber-optic scopes and airway exchange catheters (AEC) (Cook Medical, USA) are commonly used for the purpose, though various other materials have been reported in literature.[11-13]

Problems still exist with both above-mentioned "hollow" introducers and their solid counterparts used for anterograde intubation (gum elastic bougies and similar introducers made of synthetic materials). The tracheal tubes (PVC) used in daily practice have a stiffer consistency and a fixed curvature that may not negotiate the midline of mouth and pharynx or the acute pharyngo-laryngeal angle well and are known to drag relatively more flexible and redundant loop of guide (bougie, introducer, fiber-optic scope, airway exchange catheter) into the esophagus.[14] Pressures from the tip of an advancing tube can be high on points of contact with tissues, causing trauma to the airway structures.[15, 16]

Silicone-reinforced tubes follow guides more closely and easily conform to the anatomy of the upper airway. When the tip of the tube meets with an obstruction, the silicone-reinforced ones can compress and easily bend because of its flexibility and, thus, dissipate the pressure transmitted to the tip.

Another problem of railroading a tracheal tube over a guide is "snagging" of the tip of the tracheal tube at the laryngeal inlet,[18,19] which can result in delay in intubation/oxygenation, dislodgement of the tube from the larynx, esophageal intubation, and trauma to larynx and pharynx. To address this issue, equipment like inflatable introducers (AIRGUIDE™, RADLYN™), AINTREE™ catheter, and tubes with modified consistency and tips (PARKER-FLEX™ tubes, ILMA™ tubes) are used. Obtuse bevel in these tubes also help avoiding impingement on tissues causing trauma to airway structures.[17]

Several other means, like positional manipulation of head and neck, keeping the tongue out of the way with use of a laryngoscope, posterior presentation of the bevel of the tip of a tracheal tube at the laryngeal inlet,[18] and external pressure on the larynx are commonly practiced to facilitate the process of guiding.

For wire-guided intubation, sometimes another catheter with wider diameter (AINTREE™ catheter) is loaded over the first introducer (AEC, Exchange catheter or fiber-optic scope) before the tracheal tube is finally mounted over the (guide wire/introducer catheter/larger introducer) complex to build up a gradual increase in diameters between the guide wire to the tracheal tube at the tip—all for a smooth railroading process. It is apparent that presence of this rather solid complex will cause a sizable obstruction inside the larynx and trachea, making routine vital procedures like continuous delivery of Oxygen or monitoring of Capnography difficult to impossible. This guiding procedure being "blind" and used as a rescue technique in a difficult intubation situation is often performed on an awake, sedated patient. Prevention of hypoxia and monitoring the progress and placement of the endotracheal tube are essential in such a situation. Attempts to deliver Oxygen under pressure via jet ventilation through the hollow introducer catheter have been associated with barotrauma of the lungs.[2]

The problem reported with wire-guided retrograde intubation is unintentional dislodgement of the ETT from the shallow depth of insertion inside the larynx, while the retrograde guide is being taken out to insert the tracheal tube further down into the trachea. Keeping an axial pressure on the ETT that is practiced to prevent such dislodgement can have adverse physiological effects. With a modified technique using Cook retrograde intubation kit (Cook Medical, USA) in cadavers, success rate of retrograde intubation increased to 89% against 70% with the classic technique. The cause of failure in both groups was due to incorrect positioning of the endotracheal tube due to early dislodgement of the tracheal tube and the exchange catheter from the larynx.[21] This is a common problem of guiding a tracheal tube over a semi-rigid introducer.

Again, a rescue technique such as this deserves simpler instrumentation, facility for continuous delivery of Oxygen into a patient's airway, continuous capnography, and better rate of success.

Traumatic complications arising from use of semi-rigid introducers inside the airway are documented time and again in the literature.[22-27] Performance of the introducers and PVC tracheal tubes is highly variable, posing difficulty with their guiding capabilities.[28] Variability in performance is due to differences in size, manufacturing processes and ambient temperatures affecting the physical properties of the introducers.

In addition to the above academic references, a number of different endotracheal and intubation systems have been described in the patent literature. These include U.S. Patent Application publication 2009/0071484 in the name of Black et al., which discloses an endotracheal tube with a large channel for suction occupying part of main lumen; U.S. Pat. No. 4,637,389 in the name of Heyden, which discloses an endotracheal tube with a large channel eccentric to the main lumen of the tube and with an internal valve for insertion of a suction catheter; U.S. Patent Application publication 2010/0113916 in the name of Kumar, which discloses an endotracheal tube with a channel to introduce equipment probe to monitor position of the endotracheal tube; and Chinese utility patent 202096565, which discloses an endotracheal tube with an external channel for specific control of nasal intubation.

Further, a number of other proposals in the patent literature have been put forward regarding retrograde endotracheal intubation. These include Dhara and Yong (U.S. Pat. No. 5,269,769), which discloses a multi-lumen catheter guide system, not an endotracheal tube, which can hold and direct two guide wires.

Another proposal is that of Ballew (U.S. Pat. No. 4,913,139), which discloses a complex inflatable guide with a central channel for the retrograde wire over which the ETT is threaded.

Yet another system, that of Fortune (U.S. Pat. No. 5,507,279) discloses a conical tip at the end of the ETT with a short channel, which can be threaded with the retrograde wire.

In summary, several pieces of equipment and sequential steps are used to perform current techniques of wire-guided tracheal intubations. Oxygen delivery and ETCO$_2$ monitoring, two vitally essential modalities during the procedure, are difficult to achieve. Failures and complications still arise from difficulties with smooth advancement of the tracheal tubes over current methods of wire-guided intubations, particularly given the tortuous anatomy of the upper airway.

SUMMARY OF THE DISCLOSURE

While the above prior proposals may have merit, the equipment used may be complex or expensive to manufacture and/or the steps involved in carrying out the medical procedure may be time consuming or difficult.

This disclosure aims to provide a simple easy to follow a system using a single piece of equipment and a single step for wire-guided endotracheal intubation (i.e., once the guide wire is placed, only a single piece of equipment is used). The simple system provides the opportunity to deliver oxygen throughout the procedure and to monitor ETCO$_2$ to indicate the progress and correct placement of the tube. This offers unprecedented safety for management of difficult airways using wire-guided tracheal intubation techniques.

The above references to, and descriptions of, prior proposals or products are not intended to be, and are not to be construed as, statements or admissions of common general knowledge in the art.

In a first aspect, this disclosure provides an endotracheal tube for use in a wire-guided intubation procedure, the tube comprising: a) a main lumen and a sidewall; b) a proximal end portion suitable for attachment to a breathing circuit, which end portion in use protrudes from the mouth or nose of a patient; c) a distal end portion suitable for insertion into the nose and/or mouth of a patient, the distal end portion having a tip suitable for traversing the laryngeal inlet of a patient; and d) a guide housing means running between the portions having a proximal opening adjacent the proximal end portion and a distal opening adjacent to the tip, wherein the guide housing means is adjacent the sidewall of the main lumen and is suitable for slidingly receiving an anterograde or a retrograde guide during an intubation procedure to allow the tube to follow the guide into the patient.

The term "endotracheal tube" refers to a medical catheter that is inserted into the trachea through the nose or mouth in order to maintain a patent airway to deliver oxygen/artificial ventilation/anesthetic gases and vapors to a patient or to keep the tracheobronchial tree clean by removing secretions or blood.

The term "wire-guided intubation procedure" includes anterograde intubation and retrograde intubation involving a guide wire or similar piece of equipment. Anterograde intubation simply involves passing the tube over the wire through the nose or the mouth and advancing it downward into the larynx and into the trachea, the wire having been previously placed anterograde. Retrograde intubation refers to a procedure in which one end of a guide, most commonly a guide wire, is introduced from the front of the upper neck of the patient and is threaded up through the larynx and either out through the mouth or nose. The end of the guide wire is then retrieved and used as a guide to "railroad" an endotracheal tube into the larynx.

The term "breathing circuit" refers to a circuit or system that helps to connect the patient to the anesthetic gas delivery machine.

The term "having a tip suitable for traversing the laryngeal inlet of a patient" refers to an end or extremity of the distal end portion of the tube that has a suitable shape, and is made of suitably flexible material to pass smoothly through the laryngeal inlet.

The term "a guide housing means" refers to a means for enclosing, or capturing the guide such that when the endotracheal tube is pushed over the guide, the tube will be able to closely follow the path of the guide. The housing means is of a suitable shape, configuration and size that will substantially follow the long axis of the guide with little lateral movement or play.

The term "for slidably receiving a guide" refers to the guide housing means being of a size and suitable configuration to allow the endotracheal tube to slide along the guide when the guide is within the housing means.

The term "follow the guide" refers to the tube following the path or the route that the guide has taken through the anatomical spaces or structures; for example, through the center of the mouth negotiating various degrees of angular bends between the pharynx, the larynx and into the trachea, ideally without straying off course or snagging on airway structures.

The term "guide" used herein includes a guide wire and also contemplates other types of guides not made of wire.

Many other materials had been used as guides including epidural catheters or long CVP lines.

Preferably, the endotracheal tube is a flexible tube of suitable material that is reinforced along most of its length except for small sections at each end. The endotracheal tube may be made of silicon or other suitable softer non-allergenic materials.

Preferably, the tip of the distal end portion of the tube is in the form of a bevel with an appropriate angle. More preferably, the bevel is made of soft and deformable material. Even more preferably, the bevel wall and adjacent portion is devoid of reinforcing. Preferably, there are two apertures on the wall above the bevel (one on each side) to function as secondary routes to ventilation or suction on occasions of obstruction to the main opening at the distal end of the tube. These are akin to the function of a Murphy eye.

Preferably, the guide housing means is in the form of a channel or passage adjacent the main lumen sidewall of the endotracheal tube, meaning that it is eccentric to, rather than concentric with, the central axis of the main lumen. Even more preferably, the guide housing means is integrated into the sidewall of the endotracheal tube. Still more preferably, the guide housing means comprises a smooth continuous lumen.

In another aspect, the disclosure provides a kit for wire-guided endotracheal intubation comprising: i) an endotracheal tube comprising: a) a main lumen and a sidewall; b) a proximal end portion suitable for attachment to a breathing circuit, which end portion in use protrudes from the mouth or nose of a patient; c) a distal end portion for insertion into the nose and/or mouth of a patient, the distal end portion having a tip suitable for traversing the laryngeal inlet of a patient; and d) a guide housing means running between the portions having a proximal opening adjacent the proximal end portion and a distal opening adjacent to the tip, wherein the guide housing means is adjacent the sidewall of the main lumen and is suitable for slidingly receiving an anterograde or a retrograde guide during an intubation procedure to allow the tube to follow the guide into the patient and ii) a wire guide.

Preferably, the suitable guide is a guide wire.

In another aspect, the disclosure provides an improved method of endotracheal intubation comprising: i) introducing a suitable anterograde guide into the nose or mouth of a patient in a standard manner or introducing a retrograde guide by passing an end of a guide through the larynx of a patient and retrieving the end from the nose or mouth of a patient in a standard manner; ii) advancing into the patient's trachea an endotracheal tube of suitable length, wherein the tube comprises: a) a main lumen and a sidewall; b) a proximal end portion suitable for attachment to a breathing circuit; c) a distal end portion having a tip suitable for traversing the laryngeal inlet of a patient and; d) a guide housing means running between the portions having a proximal opening adjacent the proximal end portion and a distal opening adjacent to the tip, wherein the guide housing means is adjacent the sidewall of the main lumen and is suitable for slidingly receiving an anterograde or a retrograde guide during an intubation procedure to allow the tube to follow the guide into the patient; iii) wherein the tube is advanced anterograde by sliding the tube over the guide into its desired position.

The improvement resides in the fact that once the guide is in place, the design of the ETT allows it to be positioned in a single step. This saves time compared to the existing practice, especially where in current retrograde procedures, the retrograde guide is withdrawn while either pressure is exerted on the ETT to keep it in place or the guide catheter is removed from the retrograde guide and re-introduced into the lumen of the tracheal tube, all to prevent unintended displacement of the tube from the larynx. Thus, the method of this disclosure involves fewer pieces of equipment than existing methods, resulting in less potential confusion and lower costs. As the method involves fewer steps, this saves crucial time in achieving intubation. In addition, the method of the disclosure avoids certain undesirable effects of maneuvers required by current methods.

The disclosure also provides a system for an endotracheal tube insertion.

In another aspect, the disclosure provides a method of making an endotracheal tube for use in a wire-guided intubation procedure, the method comprising forming an endotracheal tube of suitable materials, the tube having a) a main lumen and a sidewall; b) a proximal end portion suitable for attachment to a breathing circuit; c) a distal end portion suitable for insertion into the nose and/or mouth of a patient, the distal end portion having a tip suitable for traversing a laryngeal inlet of a patient; and d) a guide housing means running between the portions having a proximal opening adjacent the proximal end portion and a distal opening adjacent to the tip, wherein the guide housing means is adjacent the sidewall of the main lumen and is suitable for slidingly receiving an anterograde or a retrograde guide during an intubation procedure to allow the tube to follow the guide into the patient.

Before describing the disclosure in detail, it is helpful to understand the present practice.

The current techniques of wire-guided tracheal intubation consist of: a hollow semi-rigid introducer/catheter over the guide wire already placed inside the airway; sometimes using another larger introducer catheter (AINTREE™ catheter) over the first introducer (FOS, AECs); or tracheal tube railroaded over the guide wire/introducer complex.

The problems with these protocols include: restriction of size of a tracheal tube that can be used as it is determined by outer diameter of the guide (e.g., FOS); a gap between the guide and the tracheal tube that causes difficulties with placement; pressure-(from tip of the tube) related injuries and esophageal intubation; trauma from the semi-rigid guides inside airway; failure to railroad a tracheal tube over guides every time; continuous delivery of oxygen to the patient is difficult and delivery of oxygen through the hollow guide from a high pressure source (jet) had caused barotrauma; the procedure does not have definite marker for completion of a step before proceeding to the next step.

A marker for completion of a step before proceeding to the next step provides a very important opportunity to correct a failed step immediately, thereby saving time that is crucial in preventing hypoxia or the need for an emergency surgical airway. It will be appreciated that markers of completion of steps are important in a multi-step blind procedure. For example, incorrect placement of tube is only diagnosed after guiding implements are withdrawn (except when FOS is used as guide).

Another problem is the mass of guide/larger guide/tracheal tube complex when presented at the larynx can cause sizable obstruction to the airway and it may be difficult for a patient to breathe. This problem can be even worse in a patient with a narrower larynx (laryngeal tumor) as the airway is simply plugged shut, leaving no room to breathe; the number of steps and a certain sequence involved makes the procedure lengthy and difficult.

BRIEF DESCRIPTION OF THE DRAWINGS

The disclosure will now be described with reference to the following non-limiting illustrative drawings:

FIG. 1a is a cross-sectional longitudinal view of one embodiment of the ETT;

FIG. 1b is a cross-section through the line A-A of FIG. 1a;

DETAILED DESCRIPTION

ETT 10 comprises a generally cylindrical sidewall 12 with a central lumen 15 with a central axis that runs the entire length of the tube from proximal end portion 20 to distal end portion 30. Distal end portion 30 comprises beveled end 35. Inflation tube 60, which runs partway along the length of the ETT 10, is used to inflate inflatable annular cuff 67 once tube 10 is located within the trachea to create a fluid seal.

Guide housing means 50 in the form of guiding channel 55 is located off center, or eccentrically with respect to the central axis opposite inflation tube 60 in cylindrical sidewall 12 of ETT 10. Guiding channel 55 has a smooth, continuous (un-perforated) lumen and has a proximal opening 55a at one end and distal opening 55b at the other end adjacent tip 35a. Proximal opening 55a may be sealed by stopper 56.

Figure 2:
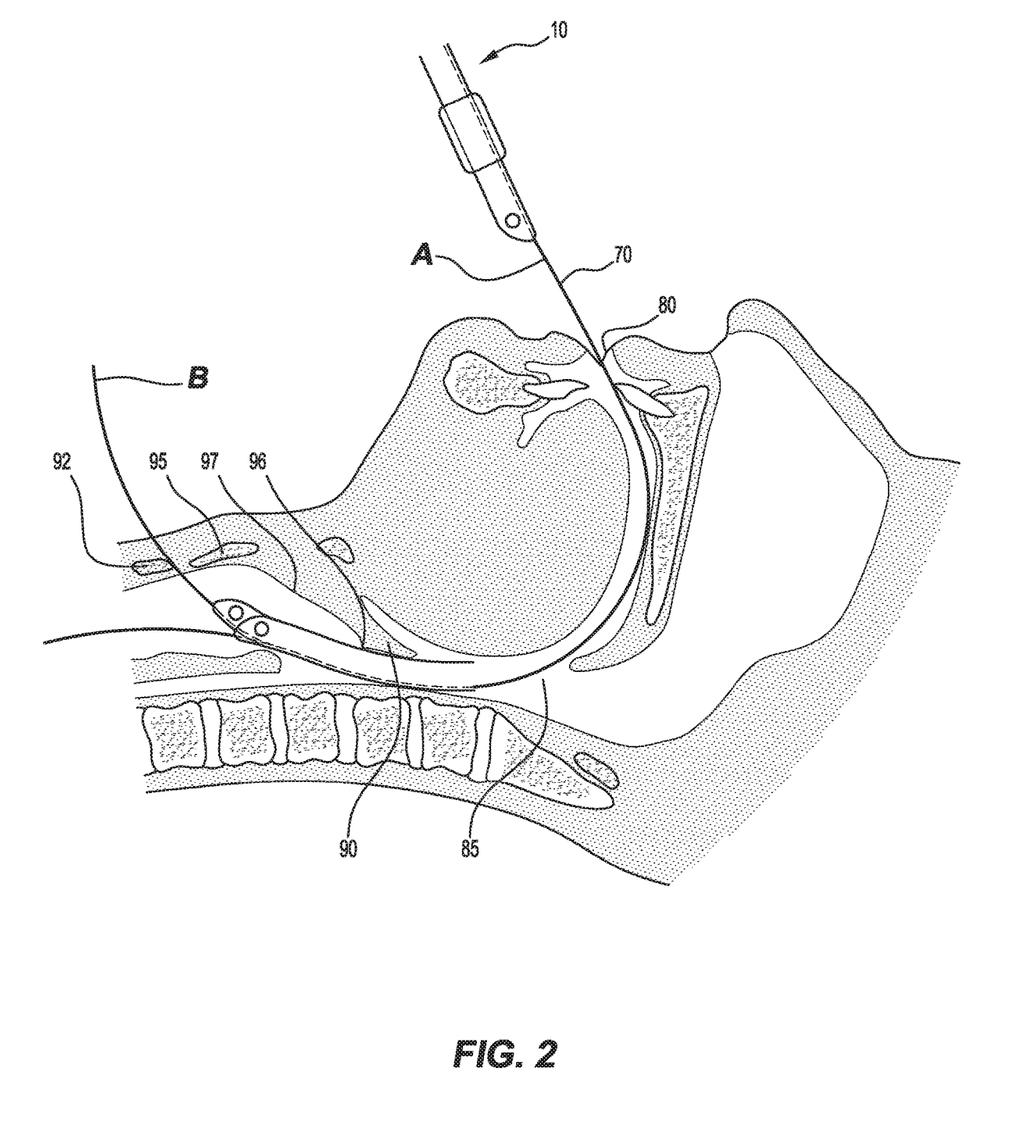
FIG. 2 is a representation of a cross-sectional view through part of a patient's head and neck showing alternative guide wire insertions (A being anterograde and B being retrograde) with the ETT railroaded over the guide prior to insertion of the ETT into the patient's mouth. The inflation cuff is omitted from the inserted tube for clarity.

The diameter of guiding channel 55 is tubular and suitable to allow sliding movement of suitable guide wire 70 within (see FIG. 2). The diameter of guiding channel 55 is wide enough to snugly accommodate a guide wire, for example, to accommodate a 0.038 inch (0.9652 mm) guide wire in a 7.5 mm tracheal tube. Suitable guide wire 70 and tube 10 have complementary flexural rigidity.

ETT 10 is provided in a suitable length for either oral or nasal placement. Generally, guiding channel 55 will run within sidewall 12 from tip 35a of beveled or slanted end 35 to where it exits the sidewall of the tube and terminates in proximal opening 55a. Inflation tube 60 exits sidewall 12 at a similar point on the opposite side.

Beveled end 35 comprises a beveled or slanted section at extreme end of distal portion 30. Tip 35a of beveled end 35 is suitable for traversing the nasal passages and the laryngeal inlet. Guiding channel 55 runs along the long axis of tube 10 from extremity of tip 35a to proximal end portion 20. Once tube 10 is threaded onto guide wire 70 via channel 55, channel 55 provides a "backbone" around which beveled end 35 may deform. The beveled portion is composed of un-reinforced material (described in more detail below), which allows both sides of the tube adjacent the extremity of tip 35a to be deformed by bending inward into the lumen of the tube making the tube particularly adapted to negotiate the laryngeal inlet. The size and shape of beveled end 35 recover quickly to the original as soon as it gets past the narrow section of the larynx 96 and enters the subglottic area.

Figures 1A, 1B:
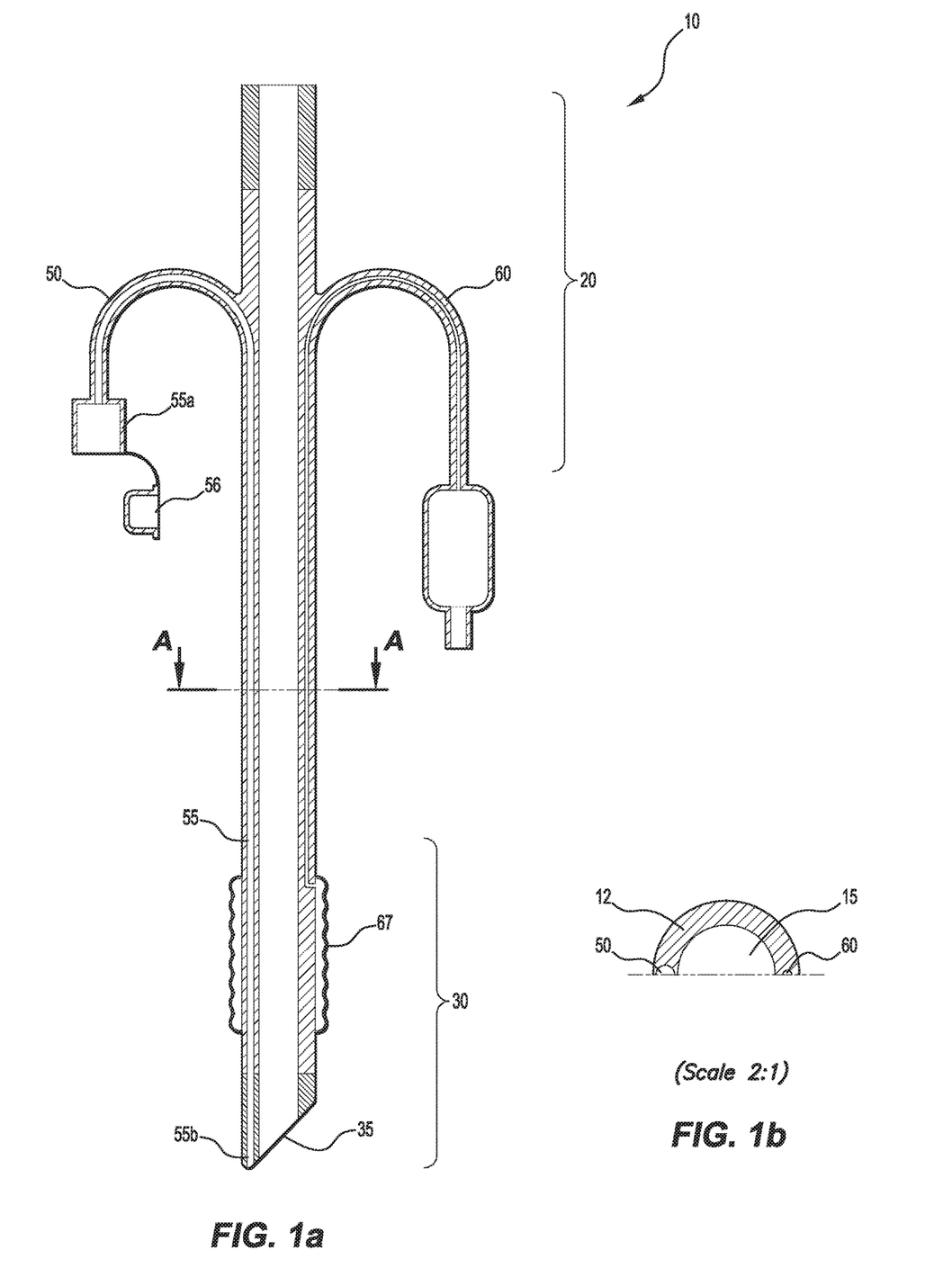
Figure 1C:
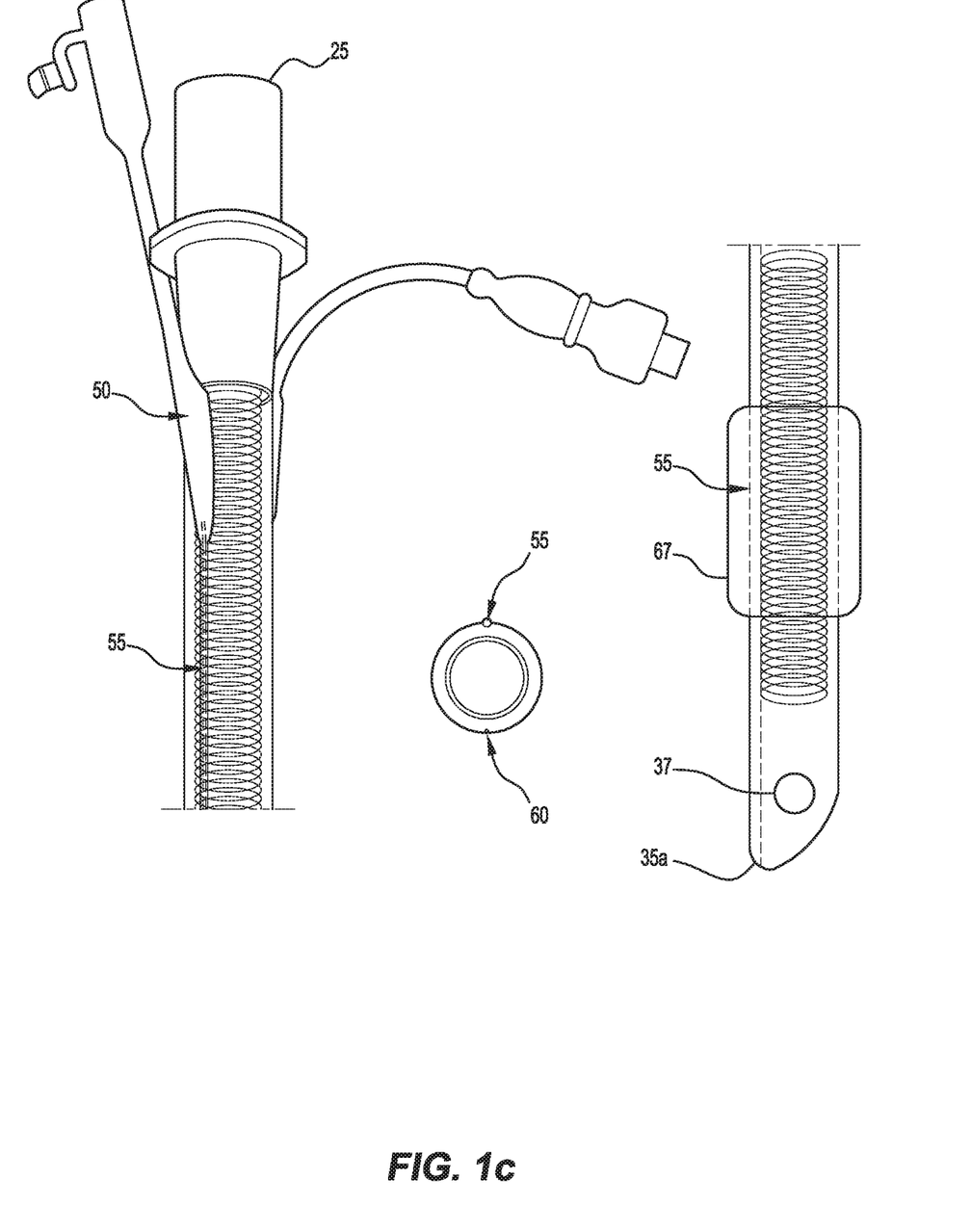
FIG. 1c is a schematic of another embodiment of the ETT.

ETT 10 comprises a reinforced section for most of its length from part of distal end portion 30 into proximal end portion 20. The reinforced section comprises a spiral metal member embedded in sidewall 12. The extreme end part of distal end portion 30 and the extreme end part of proximal end portion 20 comprise relatively short non-reinforced sections as shown by the different cross hatching in FIG. 1a and can be more clearly seen in FIG. 1c. The end 25 of proximal end portion 20 fits an intraluminal segment of a 15 mm tracheal tube connector suitable for connection to a breathing circuit or system as seen in FIG. 1c. The unreinforced end of distal portion 30 adjacent beveled end 35 is pliant and easily deformable and comprises two standard apertures 37 similar to Murphy eyes (only one shown for illustration purposes).

Persons skilled in the art of ETT production will be well versed in the manufacture of endotracheal tubes. ETT 10 may be made of any suitable material such as silicon that is non-reactive to tissues.

ETT 10 is of a suitable diameter to fit a patient's anatomy (adult or child). In the example illustrated, ETT 10 has an internal diameter of 7.5 mm with a wall thickness of 3.2 mm.

The reinforced portion of ETT 10 has a number of benefits over normal PVC ETTs. These include flexibility, which allows it to follow a retrograde guide easily across the tortuous upper airway. Where axial pressure is applied, ETT 10 does not impinge adversely on tissues causing trauma. Further, it is kink resistant. In addition, having no predetermined curve, ETT 10 can be easily rotated about its long axis.

The ETT of this disclosure is employed in intubation as follows: Thorough lubrication of the tip 35a and cuff area 67 of the ETT 10 and the guide wire 70 with suitable lubricant is performed. This is a very important step of preparation for the guiding at all times.

Suitable guide wire 70 in the form of a 0.038-inch diameter suitably coated wire is placed in the trachea 97 of a patient using one of the following techniques:

Macintosh laryngoscope (e.g., in a grade 3 Lehane and Cormack) view of the larynx 96;

Videolaryngoscope—when larynx 96 can be viewed around the bend but difficult to place a tube;

through the working channel of a flexible fiber-optic scope/flexible camera;

through an endotracheal tube in situ for exchange of ETT;

through an endotracheal tube for "trial of extubation" (staged extubation) in patients with possible postoperative airway obstruction later on;

through the space at the front of the neck between cricothyroid 95 or cricotracheal spaces or between upper tracheal rings and advanced upward in a retrograde fashion (retrograde intubation).

Specifically, in relation to the last method, after passing retrograde guide wire 70 into the patient between the thyroid and cricoid cartilages (92, 95) in the usual manner, an end thereof is retrieved from mouth 80.

The ETT 10 connected to breathing circuit with an attachment for Capnography is simply loaded over the guide wire 70 through the guiding channel 55 and advanced until the wire is out from proximal end 25. The guide wire 70 is now grabbed securely, taking care not to push or pull it in any manner. ETT 10 is railroaded by grabbing it 8-10 cm from the tip at first and then similar distance from the top (from outside the mouth) for the rest of the tube. If there is any resistance at the vocal cord level, pulling back the tube by a few millimeters and then advancing it with a rotating motion (either way) may be necessary to negotiate the larynx 96. It is a surprisingly quick, single-instrument and single-step procedure.

It should be noted that the fact that guiding channel 55 is aligned with tip 35a of tube 10 provides a convenient visual indicator of the orientation of the tip 35a.

Important advantages of the ETT of this disclosure are as follows:

It is the same familiar tracheal tube with little difference from the ones used every day in terms of primary function, form or feel;

Use of less equipment results in less costs, steps and time. Number of steps in a particular sequence for a procedure that is not done frequently will have an effect, both on learning and retaining. Time is very crucial for a rescue technique or even as a first technique of choice in a sedated/anesthetized patient;

Definite markers of progress during and after the completion of endotracheal intubation are vital for a blind guided technique. With this novel tube, $ETCO_2$ can be monitored from the fitted familiar 15 mm connector and the waveforms used to determine the progress of the tube inside the upper airway. Insertion of a thin fiber-optic scope inside the tube during railroading can easily monitor progress and confirm correct placement of the tube inside the trachea;

Continuous delivery of oxygen throughout the procedure is possible by connecting the tube to a source of oxygen, namely, an anesthetic breathing system;

Clinician is not restricted to use a particular size of tracheal tube (as opposed to wire-guided intubation over the fiber-optic scope in children);

Damage to the suction channel of a fiber-optic scope caused by the guide wire can be avoided by using the channel in the tube instead. The fiberscope may be inserted inside the main lumen of the tube for monitoring the progress and position of the tube inside the airway;

the concept is applicable to both children and adults;

airway is unobstructed by the tube throughout the process of wire-guided intubation because the central lumen is not occupied by introducers as in some of the prior art.

EXAMPLE 1: INTUBATION STUDY

After initial bench testing on physical models and dedicated airway simulator (AIRSIM®, Laerdal), the behavior of the prototypes were observed in dissected, intact and fresh cadavers.

The snug relationship of diameters between a guide wire and the guiding channel ensure that the deformations in both are identical at all times during the process of railroading. This way, the pushing force applied on the upper part of the tube translates only to progress of the tip of the tube forward and is not wasted, as in a case of a guide through the main channel of a tube, in random lateral bending or snagging on structures on the way.

The trajectory of the tip of the advancing tube is solely determined by the guide wire inside the airway.

The soft non-reinforced section at the tip of the tube, while negotiating the vocal cords, deforms inward to a smaller size but readily re-expands inside the wider subglottic space.

Thorough lubrication of the tip and cuff area of the tracheal tube and the guide wire with suitable lubricant is a very important step of preparation for the guiding at all times.

Progress of the tube inside the airway were observed and recorded using a flexible camera (AMBU®) or a fiber-optic scope (Olympus) from the mouth, from below the vocal cords and through the main lumen of the tube.

Fluoroscopic video of wire-guided intubation using this tube was recorded to illustrate the way it advances along the airway. The tube was found to follow the guide wire across the entire upper airway smoothly without straying.

During retrograde tracheal intubation on cadavers, even while using cricothyroid membrane puncture (shallow depth of insertion), the soft, neutral tube could easily be stabilized inside the larynx during removal of guide wire.

This disclosure is related to Australian provisional patent applications No. 2013903646 and 2014901331 filed 23 Sep. 2013 and 11 Apr. 2014, respectively, the specifications of which are herein incorporated by reference.

Throughout this specification and the claims that follow, unless the context requires otherwise, the words "comprise," "comprises," and "comprising" will be understood to mean the inclusion of the stated integer, step or group of integers or steps but not the exclusion of any of other integers, step or group of integers or steps.

TABLE 1

Parts List
Reference numeral
Feature

| | |
|---|---|
| 10 | Endotracheal tube |
| 12 | Tube wall |
| 15 | Central lumen |
| 20 | Proximal end portion |
| 25 | End of proximal end portion |
| 30 | Distal end portion |
| 35 | Beveled end |
| 35a | Tip of beveled end |
| 37 | Apertures |
| 50 | Guide wire housing |
| 55 | Guiding channel |
| 55a | Proximal opening of guide wire channel |
| 55b | Distal opening of guide wire channel |
| 56 | Stopper |
| 60 | Inflation tube |
| 67 | Annular inflation cuff |
| 70 | Guide wire |
| 80 | Mouth |
| 85 | Pharynx |
| 90 | Epiglottis |
| 92 | Thyroid cartilage |
| 95 | Cricoid cartilage |
| 96 | Larynx |
| 97 | Trachea |

REFERENCES

1. Stiles C. M. A flexible fiber-optic bronchoscope for endotracheal intubation of infants. *Anesth. Analg.* 1974; 53 (6):1017-1019.
2. Cooper J. R. Use of a LMATM and a sequential technique for unanticipated difficult intubations. *Anesthesiology* 2002; 97(5):1326.
3. Joffe A. M., G. A. Arndt, and K. William. Wire guided catheter exchange after failed direct laryngoscopy in critically ill adults. *J. Clin. Anesth.* 2010; 22:93-5.
4. Matioc A. A. Use of the Arndt airway exchanger catheter set with the laryngeal mask airway supreme. *J. Clin. Anesth.* 2009; 21:152-3.
5. Yurino M. Retrograde and antegrade intubation techniques under general anaesthesia through the laryngeal mask airway.
6. Dhara S. S. Retrograde tracheal intubation. 2009; 64:1094-1104.
7. Scherlitz A. and J. Peters. Translaryngeal fiber-optic insertion of a guidewire into the trachea to assist fiber-optic reintubation in patients with a difficult airway. *Anaesthetist* 1994; 43:618-620.
8. Hartmannsgruber M. W., and S. H. Rosenbaum. Safer endotracheal tube exchange technique. *Anesthesiology* 1998; 88:1683.

9. Benumof J. L. Additional safety measures when changing endotracheal tubes. *Anesthesiology* 1991; 75(5):921.
10. Pujari V., S. Shivanna, and Y. Bevinaguddiah. Wire aided reintubation following rigid bronchoscopy: A safe technique. *Indian Paediatrics* 2012; 49:983-84.
11. Telford R. J., J. F. Searle, R. W. Boaden, and F. Baier. Use of a guidewire and a ureteral dilator as an aid to awake fiber-optic intubation. *Anaesthesia* 1994; 49:691-693.
12. Warrillow S. Difficult intubation managed using standard laryngeal mask airway, flexible fiber-optic bronchoscope and wire guided enteral feeding tube. *Anaesth. Intensive Care* 2005; 33:659-661.
13. Rajan G. R. Fiber-optic wire-guided transoral and through the LMA intubation technique using modified gum elastic bougie. *Anesth. Analg.* 2005; 100:599-600.
14. Moorthy S. S., and S. F. Dierdorf. An unusual difficulty in fiber-optic intubation. *Anesthesiology* 1985; 63:229.
15. Hwan S. J., M. T. Kataoka, J. B. C. Roberts, J. Doyle, and C. D. Mazer. PVC tracheal tubes exert forces and pressures seven to ten times higher than silicone or armoured tracheal tubes—an in vitro study. *Can. J. Anesth.* 2002; 49(9):986-989.
16. Wissler R. N., N. Gravenstein, and M. J. Banner. Wire-reinforced endotracheal tubes: composition affects the response to external compression and kinking (Abstract). *Anesthesiology* 1991; 75 (3A):A394.
17. Brull S. J., R. Wiklund, C. Ferris, N. R. Connelly, J. Ehrenworth, and D. G. Silverman. Facilitation of fiber-optic orotracheal-intubation with a flexible tracheal tube. *Anesth. Analg.* 1994; 78; 746-8.
18. Cossham P. S. Difficult intubation. *Br. J. Anaesth.* 1985; 57:239.
19. Higgs A., David R. Swamipillai, Patel A. Mitchell, and M. Popat. Re-intubation over airway exchange catheters—mind the gap. *Anaesthesia* 2010; 65:859-60.
20. Benumof J. L. Airway exchange catheters for safe extubation. The Clinical and scientific details that make the concept work. *Chest* 1997; 111(6):1483-6.
21. Lenfant F., M. Benkhadra, P. Trouilloud, and M. Freysz. Comparison of two techniques for retrograde tracheal intubation in human fresh cadavers. *Anesthesiology* 2006; 104:48-51.
22. Hagberg C., and R. Georgi. Complications of managing the airway. *Best Practice & Research Clinical Anaesthesiology* 2005; 19(4): 641-659.
23. Bogod D., and M. Popat. NAP4 Report and findings of the 4th National Audit Project of The Royal College of Anaesthetists. 2011. Chapter 12 *Tracheal Intubation* P 96-104.
24. Evans H., I. Hodzovic, and I. P. Latto IP. Tracheal tube introducers: choose and use with care. *Anaesthesia* 2010; 65:859.
25. Prabhu A., P. Pradhan, R. Sanaka, and A. Bilolikar. Bougie trauma—it is still possible. *Anaesthesia* 2003; 58:811-813
26. Kadry M., and M. Popat. Pharyngeal wall perforation—an unusual complication of blind intubation with gum elastic bougie. *Anaesthesia* 1999: 54:404-5.
27. Gardner M., and S. Janokwski. Detachment of the tip of a gum-elastic bougie. *Anaesthesia* 2002; 57:88-89
28. Hodzovic I., and I. P. Latto. Single use tracheal introducers may not be fit for purpose. *Anaesthesia* 2007; 62:1189-90.

What is claimed is:

1. An endotracheal tube for use in a wire-guided intubation procedure, the endotracheal tube comprising:

a main lumen having a sidewall, the main lumen composed of a flexible material and having a flexural rigidity complementary to a flexural rigidity of an anterograde or retrograde guide wire so as to slidingly follow the guide wire and therefore follow the shape of an airway path along which the previously located guide wire extends in use into the patient's trachea, the main lumen having the flexible material of most of its length reinforced so as to prevent kinking thereof during intubation, use, and extubation;

a proximal end portion of the main lumen having an end for attachment to a breathing circuit, which proximal end portion, in use, is configured to protrude from the patient's mouth or nose;

a distal end portion of the main lumen for insertion in use into the patient's nose and/or mouth for entrance into the patient's airway in a direction leading to the patient's trachea, wherein the flexible material of which an extreme end part of the distal end portion is composed is non-reinforced and is soft so as to be more readily deformable relative to the reinforced material, the extreme end part of the distal end portion having a beveled end with a tip that is shaped and is deformable for traversing the patient's laryngeal inlet during the wire-guided intubation procedure; and a tubular guide channel defined by a smooth continuous un-perforated lumen within the sidewall of the main lumen and extending from a proximal opening of the tubular guide channel from which the tubular guide channel extends to pass laterally into the sidewall at the proximal end portion and spaced from the end for attachment to the breathing circuit to a distal opening of the tubular guide channel in the tip, wherein the tubular guide channel in use is configured to slidingly receive, during the wire-guided intubation procedure, the guide wire that in use extends into the patient's trachea from the patient's mouth or nose and which extends in through the proximal opening of the tubular guide channel, along the tubular guide channel, and out through the distal opening of the tubular guide channel, wherein the guide wire and the tubular guide channel have respective diameters such that the guide wire is snugly accommodated in the tubular guide channel, whereby the complementary flexural rigidity of the endotracheal tube and the guide wire and the snug accommodation of the guide wire in the tubular guide channel ensure that deformations in both the endotracheal tube and guide wire are identical at all times so that the tip in use slidingly follows the guide wire into the patient's trachea, and the main lumen throughout its length from the distal end portion to the proximal end portion in use follows the guide wire passing along the entire length of the tubular guide channel thereby following the shape of the airway path.

2. The endotracheal tube of claim 1, wherein the soft material of which the extreme end part of the distal end portion is composed allows both sides of the endotracheal tube at the tip to deform inwardly to a smaller size as the tip in use is moved past the laryngeal inlet of the patient and to return to its original shape as it moves into the subglottic area of the patient.

3. The endotracheal tube of claim 1, which is absent a predetermined curve.

4. A method for endotracheal intubation of a patient, the method comprising the steps of:

locating a guide wire having a flexural rigidity throughout an airway path of the patient from the trachea of the patient to the nose or mouth of the patient by introducing the guide wire in an anterograde manner into the nose or mouth of the patient and advancing it anterograde through the larynx and into the trachea of the patient leaving an end of the guide wire outside the nose or mouth of the patient, or by introducing the guide wire in a retrograde manner by passing an end of the guide wire through the front of the neck of the patient into the larynx of the patient and advancing it retrograde and retrieving the end so that the end is outside the nose or mouth of the patient; and subsequently advancing into the patient's trachea an endotracheal tube of suitable length, wherein the endotracheal tube comprises:

a main lumen having a sidewall, the main lumen being composed of a flexible material and having a flexural rigidity complementary to the flexural rigidity of the guide wire so as to slidingly follow the guide wire and therefore follow the shape of the airway path, along which the previously located guide wire extends into the trachea of the patient, the main lumen having the flexible material of most of its length reinforced to prevent kinking thereof during its intubation, use, and extubation;

a proximal end portion having an end for attachment to a breathing circuit, and which end portion is configured to protrude in use from the mouth or nose of the patient;

a distal end portion of the main lumen for insertion into the nose and/or mouth of the patient so as to enter the airway in the direction leading to the trachea, wherein the flexible material of which an extreme end part of the distal end portion is composed is non-reinforced and is soft so as to be more readily deformable relative to the reinforced material, the extreme end part of the distal end portion having a beveled end with a tip shaped and deformable for traversing the laryngeal inlet of the patient during the endotracheal intubation of the patient; and a tubular guide channel defined by a smooth continuous un-perforated lumen within the sidewall of the main lumen and extending from a proximal opening of the tubular guide channel from which the tubular guide channel extends to pass laterally into the sidewall at the proximal end portion and spaced from the end for attachment to the breathing circuit to a distal opening of the tubular guide channel in the tip, wherein the tubular guide channel is configured to slidingly receive during the endotracheal intubation of the patient the guide wire extending into the trachea of the patient from the mouth or nose of the patient and which extends in through the proximal opening of the tubular guide channel, along the tubular guide channel, and out through the distal opening of the tubular guide channel, wherein the guide wire and the tubular guide channel have respective diameters such that the guide wire is snugly accommodated in the tubular guide channel, whereby the complementary flexural rigidity of the endotracheal tube and the guide wire and the snug accommodation of the guide wire in the tubular guide channel ensure that deformations in both the endotracheal tube and guide wire are identical at all times so that the tip slidingly follows the guide wire into the trachea of the patient;

wherein the step of advancing into the patient's trachea the endotracheal tube comprises loading the endotracheal tube into the guide wire by passing the proximal end of the guide wire that is outside of the nose or mouth of the patient into the distal opening of the tubular guide channel in the tip and railroading the endotracheal tube along the guide wire until the proximal end of the guide wire emerges from the proximal opening of the tubular guide channel, holding the end of the guide wire that emerges from the proximal end of the tubular guide channel, and advancing the endotracheal tube in an anterograde direction by sliding the tubular guide channel over the guide wire so that the main lumen throughout its length from the distal end portion to the proximal end portion follows the guide wire passing along the length of the tubular guide channel thereby following the shape of the airway path until the tip at the distal end portion of the main lumen has advanced into its desired position into the trachea of the patient.

5. The method according to claim 4, wherein the soft material of which the extreme end part of the distal end portion is composed allows both sides of the endotracheal tube at the tip to deform inwardly to a smaller size as the tip is moved past the laryngeal inlet of the patient and to return to its original shape as it moves into the subglottic area of the patient.

6. An assembly of a guide wire and an endotracheal tube for wire-guided endotracheal intubation of a patient, the assembly comprising:

a guide wire having a flexural rigidity and which in use is installed through the airway of the patient in anterograde or a retrograde manner so that the guide wire extends from the patient's trachea to an end of the guide wire outside the mouth or nose of the patient; and an endotracheal tube comprising:

a main lumen having a sidewall, the main lumen being composed of a flexible material and having a flexural rigidity complementary to the flexural rigidity of the guide wire so as to slidingly follow the guide wire and therefore follow the shape of the patient's airway path along which the guide wire extends in use, into the trachea of the patient, the main lumen having the flexible material of most of its length reinforced to prevent kinking thereof during its intubation, use, and extubation;

a proximal end portion of the main lumen having an end for attachment to a breathing circuit, and which proximal end portion, in use, is configured to protrude from the patient's mouth or nose;

a distal end portion of the main lumen for insertion into the nose and/or mouth of the patient so as to enter the airway in the direction leading to the trachea, wherein the flexible material of which the distal end portion is composed is non-reinforced and is soft as to be more readily deformable relative to the reinforced material, the distal end portion having a beveled end with a tip, which is shaped and is deformable for traversing the laryngeal inlet of the patient during the wire-guided endotracheal intubation of the patient; and a tubular guide channel defined by a smooth continuous un-perforated lumen within the sidewall of the main lumen and extending from a proximal opening of the tubular guide channel from which the tubular guide channel extends to pass laterally into the sidewall at the proximal end portion and spaced from the end for attachment to the breathing circuit to a distal opening of the tubular guide channel in the tip, wherein the tubular guide channel has slidingly received therethrough the guide wire so that the guide wire extends in through the proximal opening of the tubular guide channel, throughout the length of the tubular guide channel, and emerges out through the distal opening of the tubular guide channel in the tip of the endotracheal tube, wherein the guide wire and the tubular guide channel have respective diameters such that the guide wire is snugly accommodated in the tubular guide channel, whereby the complementary flexural rigidity of the endotracheal tube and the guide wire and the snug accommodation of the guide wire in the tubular guide channel ensure that deformations in both the endotracheal tube and guide wire are identical at all times so that the tip in use slidingly follows the guide wire into the patient's trachea, and whereby the guide wire that extends from and beyond the tip of the distal end portion of the endotracheal tube and which in use extends into the patient's trachea guides the tip to follow the guide wire into the patient's trachea, and whereby the main lumen throughout its length from the distal end portion to the proximal end portion in use follows the guide wire passing along the entire length of the tubular guide channel thereby following the shape of the airway path.

7. The assembly of claim 6, wherein the endotracheal tube is absent a predetermined curve.

8. The assembly of claim 6, wherein the soft material of which the extreme end part of the distal end portion is composed allows both sides of the endotracheal tube at the tip to deform inwardly to a smaller size as the tip in use is moved past the patient's laryngeal inlet and to return to its original shape as it moves into the subglottic area of the patient.

9. A method for endotracheal intubation of a patient, the method comprising the steps of:

locating a guide wire having a flexural rigidity throughout an airway path of the patient from the trachea of the patient to the nose or mouth of the patient by introducing the guide wire in an anterograde manner into the patient's nose or mouth and advancing it anterograde through the larynx and into the trachea of the patient leaving an end of the guide wire outside the nose or mouth of the patient, or by introducing the guide wire in a retrograde manner by passing an end of the guide wire through the front of the neck of the patient into the larynx of the patient and advancing it retrograde and retrieving the end so that the end is outside the nose or mouth of the patient and subsequently advancing into the patient's trachea an endotracheal tube of suitable length, wherein the endotracheal tube comprises:

a main lumen having a sidewall, the main lumen being composed of a flexible material and having a flexural rigidity complementary to the flexural rigidity of the guide wire so as to slidingly follow the guide wire and therefore follow the shape of the airway path, along which the previously located guide wire extends into the trachea of the patient, the main lumen having the flexible material of most of its length reinforced to prevent kinking thereof during its intubation, use, and extubation;

a proximal end portion having an end for attachment to a breathing circuit, and which end portion is configured to protrude in use from the mouth or nose of the patient;

a distal end portion of the main lumen for insertion into the nose and/or mouth of the patient so as to enter the airway in the direction leading to the trachea, wherein the flexible material of which an extreme end part of the distal end portion is composed is non-reinforced and is soft so as to be more readily deformable relative to the reinforced material, the extreme end part of the distal end portion having a beveled end with a tip shaped and deformable for traversing the laryngeal inlet of the patient during the endotracheal intubation of the patient; and a tubular guide channel defined by a smooth continuous un-perforated lumen within the sidewall of the main lumen and extending from a proximal opening of the tubular guide channel from which the tubular guide channel extends to pass laterally into the sidewall at the proximal end portion and spaced from the end for attachment to the breathing circuit to a distal opening of the tubular guide channel in the tip, wherein the tubular guide channel is configured to slidingly receive during the endotracheal intubation of the patient the guide wire extending into the trachea of the patient from the mouth or nose of the patient and which extends in through the proximal opening of the tubular guide channel, along the tubular guide channel, and out through the distal opening of the tubular guide channel, wherein the guide wire and the tubular guide channel have respective diameters such that the guide wire is snugly accommodated in the tubular guide channel, whereby the complementary flexural rigidity of the endotracheal tube and the guide wire and the snug accommodation of the guide wire in the tubular guide channel ensure that deformations in both the endotracheal tube and guide wire are identical at all times so that the tip slidingly follows the guide wire into the trachea of the patient;

wherein the step of advancing into the patient's trachea the endotracheal tube comprises connecting the end of the proximal end portion of the endotracheal tube to the breathing circuit to enable breathing of the patient is possible through the main lumen during further steps to effect intubation of the patient, and subsequent to the step of connecting the endotracheal tube to the breathing circuit:

loading the endotracheal tube into the guide wire by passing the proximal end of the guide wire that is outside of the nose or mouth of the patient into the distal opening of the tubular guide channel in the tip and railroading the endotracheal tube along the guide wire until the proximal end of the guide wire emerges from the proximal opening of the tubular guide channel, holding the end of the guide wire that emerges from the proximal end of the tubular guide channel, and advancing the endotracheal tube in an anterograde direction by sliding the tubular guide channel over the guide wire so that the main lumen throughout its length from the distal end portion to the proximal end portion follows the guide wire passing along the length of the tubular guide channel thereby following the shape of the airway path until the tip at the distal end portion of the main lumen has advanced into its desired position into the trachea of the patient.

\* \* \* \* \*